United States Patent
Sandstrom et al.

(10) Patent No.: US 9,629,610 B2
(45) Date of Patent: Apr. 25, 2017

(54) METHOD OF OPERATING ULTRASOUND DIAGNOSIS APPARATUS FOR PROVIDING MAP OF INTEREST INDEX AND ULTRASOUND DIAGNOSIS APPARATUS USING THE METHOD

(75) Inventors: Kurt Sandstrom, Seoul (KR); Tae-yun Kim, Seoul (KR); Yoon-chang Lee, Jeongeup-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 116 days.

(21) Appl. No.: 13/335,106

(22) Filed: Dec. 22, 2011

(65) Prior Publication Data

US 2012/0184849 A1   Jul. 19, 2012

(30) Foreign Application Priority Data

Dec. 22, 2010 (KR) .................. 10-2010-0132633
Nov. 28, 2011 (KR) .................. 10-2011-0125211

(51) Int. Cl.
  *A61B 8/00* (2006.01)
  *A61N 7/00* (2006.01)
  *A61B 8/08* (2006.01)
  *G01S 7/52* (2006.01)

(52) U.S. Cl.
  CPC ............... *A61B 8/485* (2013.01); *A61B 8/48* (2013.01); *G01S 7/52071* (2013.01); *A61B 8/0891* (2013.01); *G01S 7/5205* (2013.01)

(58) Field of Classification Search
  CPC .................. A61N 7/022; A61N 2007/0078
  USPC ....................................................... 600/437
  See application file for complete search history.

(56) References Cited

U.S. PATENT DOCUMENTS

| 5,509,413 | A | 4/1996 | Akama et al. |
| 6,413,218 | B1 * | 7/2002 | Allison et al. ............. 600/443 |
| 6,824,518 | B2 * | 11/2004 | Von Behren et al. ....... 600/443 |
| 2006/0030779 | A1 | 2/2006 | Chomas et al. |
| 2007/0196282 | A1 * | 8/2007 | Oliver ......................... 424/9.52 |
| 2007/0255267 | A1 * | 11/2007 | Diederich et al. ............. 606/27 |

(Continued)

FOREIGN PATENT DOCUMENTS

| JP | 3378308 B2 | 2/2003 |
| JP | 2009-142474 * | 2/2009 ............... A61B 8/08 |

(Continued)

OTHER PUBLICATIONS

"Tsuda et al.," "Nonlinear Interpolation of Multivariable Functions by the Monte Carlo Method," Journal of the Association for Computing Machinery, vol. 17, No. 3, pp. 420-425, 1970.*

(Continued)

*Primary Examiner* — Tse Chen
*Assistant Examiner* — Patricia Park
(74) *Attorney, Agent, or Firm* — McDermott Will & Emery LLP

(57) ABSTRACT

An ultrasound diagnosis apparatus providing a map of an interest index. The ultrasound diagnosis apparatus includes: a calculating unit for calculating a mechanical index (MI) corresponding to a depth value in a direction in which ultrasound travels from an ultrasound output part of a transmission transducer; a visualization unit for generating an MI map in which a relationship between the calculated MI and the depth value is visualized in the form of a graph; and a display unit for displaying the MI map.

15 Claims, 4 Drawing Sheets

(56) References Cited

U.S. PATENT DOCUMENTS

| | | |
|---|---|---|
| 2008/0139942 A1* | 6/2008 | Gaud et al. ............... 600/458 |
| 2009/0036772 A1* | 2/2009 | Lu .............................. 600/437 |
| 2009/0088623 A1* | 4/2009 | Vortman et al. ........... 600/411 |
| 2009/0099482 A1* | 4/2009 | Furuhata et al. ............... 601/2 |
| 2009/0171215 A1 | 7/2009 | Kato et al. |
| 2010/0068260 A1* | 3/2010 | Kruse et al. ................ 424/450 |
| 2010/0241036 A1* | 9/2010 | Vortman et al. ............... 601/3 |
| 2011/0060221 A1* | 3/2011 | Fan et al. .................... 600/438 |

FOREIGN PATENT DOCUMENTS

| | | |
|---|---|---|
| JP | 2009-142474 A | 7/2009 |
| JP | 2009-153674 A | 7/2009 |
| KR | 10-2010-0016740 A | 2/2010 |

OTHER PUBLICATIONS

"Ziskin," "The Thermal Dose Index," J. Ultrasound Med Oct. 2010; 29(10): 1475-1479.*
International Search Report issued in International Patent Application No. 11195229.7 dated May 23, 2012.
Korean Non-Final Office in Korean Application No. 10-2011-0125211, dated Dec. 20, 2012.
Korean Office Action with English translation issued in Korean Application No. 10-2011-0125211 mailed Jun. 27, 2013.
Korean Notice of Allowance with English translation issued in Korean Application No. 10-2011-0125211 mailed Sep. 4, 2013.

\* cited by examiner (a)                    (b)

METHOD OF OPERATING ULTRASOUND DIAGNOSIS APPARATUS FOR PROVIDING MAP OF INTEREST INDEX AND ULTRASOUND DIAGNOSIS APPARATUS USING THE METHOD

CROSS-REFERENCE TO RELATED PATENT APPLICATION

This application is a continuation-in-part of U.S. patent application Ser. No. 13/092,573, filed on Apr. 22, 2011 and claims the benefit of Korean Patent Application Nos. 10-2010-0132633, filed on Dec. 22, 2010, 10-2011-0125211, filed on Nov. 28, 2011, in the Korean Intellectual Property Office, the disclosures of which are incorporated herein in their entirety by reference.

BACKGROUND OF THE INVENTION

1. Field of the Invention

The present invention relates to an ultrasound diagnosis apparatus for providing a map of an interest index, and more particularly, to an ultrasound diagnosis apparatus for providing at least one of a mechanical index (MI) map, an acoustic pressure map, and a thermal index (TI) map according to various standards such as a depth value, a scan line, time, and the like, and an ultrasound diagnosis method.

2. Description of the Related Art

Ultrasound diagnosis apparatuses transmit an ultrasound signal toward a predetermined part of the body from a body surface of an object and obtain a tomogram of soft-tissues or an image of blood flow by using information regarding the ultrasound signal reflected by tissues of the body.

Ultrasound diagnosis apparatuses have various advantages, for example, a compact size, low cost, and real-time display. Also, ultrasound diagnosis apparatuses have excellent stability because there is no fear of radiation exposure, and thus, the ultrasound diagnosis apparatuses are widely used together with various other diagnosis apparatuses, such as computerized tomography scanners, magnetic resonance imaging (MRI) apparatuses, nuclear medicine diagnosis apparatuses, or the like.

In general, the output (a transmission voltage, pressure, and energy) of an ultrasound diagnosis apparatus is limited by an international standard, for example, a mechanical index (MI), and is determined. In this regard, the MI is an index that represents quantified mechanical effects of ultrasound on a human body.

The international standard also includes a thermal index (TI). As well known, international acceptable standards of the MI and the TI are less than 1.9 and less than 6.0, respectively.

Ultrasound diagnosis apparatuses increase a transmission voltage of an ultrasound signal that is output from a pulsar to more accurately diagnose an object. As the transmission voltage of the ultrasound signal is increased, image sensitivity improves, while an MI or acoustic pressure may be increased.

A high MI (or acoustic pressure) means that an ultrasound diagnosis apparatus has a greater effect on a human body. Also, if the MI (or acoustic pressure) is increased over a predetermined level, the use of the corresponding ultrasound diagnosis apparatus is restricted by an international standard.

In consideration of such a problem, a transmission voltage of an ultrasound diagnosis apparatus needs to be accurately controlled to sufficiently increase the transmission voltage and to maintain an MI, acoustic pressure, and a TI, which are interest indexes, having values less than a threshold value.

However, recently, only an interest index of a reference value that is simply represented numerically is provided without careful consideration to a value of a depth of interest, which is a distance in a direction in which ultrasound travels from a pulse output part of an ultrasound diagnosis apparatus to a part to be diagnosed. In other words, there is provision of visualized data about an interest index that is necessary for a user of an ultrasound diagnosis apparatus to control a transmission voltage in order to increase image sensitivity.

SUMMARY OF THE INVENTION

The present invention provides a method used to increase image quality and satisfy an international mechanical index (MI) standard by providing an MI according to a depth of interest in the form of a map and allowing a user to easily confirm the MI visually in order to control configurable values such as transmission output, and an ultrasound diagnosis apparatus using the method.

The present invention also provides a method used to increase image quality and allow a user to conveniently control configurable values of the ultrasound diagnosis apparatus by visually providing an acoustic pressure map or a thermal index (TI) map in addition to the MI map, and an ultrasound diagnosis apparatus using the method.

According to an aspect of the present invention, there is provided an ultrasound diagnosis apparatus including: a calculating unit for calculating a mechanical index (MI) corresponding to a depth value in a direction in which ultrasound travels from an ultrasound output part of a transmission transducer; a visualization unit for generating an MI map in which a relationship between the calculated MI and the depth value is visualized in the form of a graph; and a display unit for displaying the MI map.

The calculating unit may select a plurality of the depth values, calculates MIs respectively corresponding to the plurality of depth values, and interpolates non-calculated MIs corresponding to depth values in a direction in which ultrasound travels by using MIs corresponding to the calculated depth values.

The calculating unit may further calculate an acoustic pressure value corresponding to depth values in a direction in which ultrasound travels from the ultrasound output part of the transmission transducer; the visualization unit further generates an acoustic pressure map in which a relationship between the calculated acoustic pressure value and the depth value is visualized in the form of a graph; and the display unit selectively displays the MI map or the acoustic pressure map.

The calculating unit may further calculate a thermal index (TI) corresponding to a depth value in which ultrasound travels from the ultrasound output part of the transmission transducer; the visualization unit further generates a TI map in which a relationship between the calculated TI and the depth value is visualized in the form of a graph; and the display unit selectively displays the MI map or the TI map.

The TI map may include at least one selected from the group consisting of a Bone TI (TIb) map, a Cranial bone TI (TIc) map, and a Soft tissue TI (TIs) map, and the display unit selects any one selected from the group consisting of the TIb map, the TIc map, and the TIs map and displays the selected map.

The calculating unit may further calculate a thermal dose obtained by accumulating the TI according to time; the visualization unit further generates a thermal dose map in which the calculated thermal dose is visualized in the form of a graph; and the display unit displays at least one selected from the group consisting of the TI map and the thermal dose map.

The ultrasound diagnosis apparatus may further include an alarm unit for outputting an alarm signal when the calculated MI or the calculated acoustic pressure value exceeds a predetermined range.

The MI map or the TI map may be a two-dimensional or three-dimensional map.

The ultrasound diagnosis apparatus may further include a receiving unit for receiving selection with respect to an attenuation coefficient, and the calculating unit calculates an MI corresponding to a depth value in consideration of the selected attenuation coefficient. The ultrasound diagnosis apparatus may further include a controller for controlling a transmission voltage based on the selected attenuation coefficient. The attenuation coefficient may be selected based on characteristics of tissues of an object.

The ultrasound diagnosis apparatus may further include a receiving unit for obtaining information regarding a contrast agent injected into an object, and the visualization unit generates an acoustic pressure map including a threshold value due to a vibration characteristic of the contrast agent injected into the object. The threshold value may include at least one selected from the group consisting of a linear vibration threshold value, a non-linear vibration threshold value, and a breaking vibration threshold value.

The ultrasound diagnosis apparatus may further include a controller for controlling a transmission voltage based on a threshold value due to a vibration characteristic of the contrast agent injected into the object.

The ultrasound diagnosis apparatus may include: a receiving unit for receiving selection of a first region, which is a region of interest (ROI), in a ultrasound diagnosis region of an object; and a controller for controlling a transmission voltage of the first region to a first transmission voltage so as to maintain an MI or an acoustic pressure value in the first region within a predetermined threshold range. The controller controls a transmission voltage of a second region so that a transmission voltage of the second region other than the ROI in the ultrasound diagnosis region of the object is below the first transmission voltage.

The display unit may output an ultrasound image of blood vessel tissues including a contrast agent with respect to the first region, and outputs an ultrasound image of general tissues with respect to the second region.

According to another aspect of the present invention, there is provided a method of operating an ultrasound diagnosis apparatus, the method including: calculating a mechanical index (MI) corresponding to a depth value in a direction in which ultrasound travels from an ultrasound output part of a transmission transducer; generating an MI map in which a relationship between the calculated MI and the depth value is visualized in the form of a graph; and displaying the MI map.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
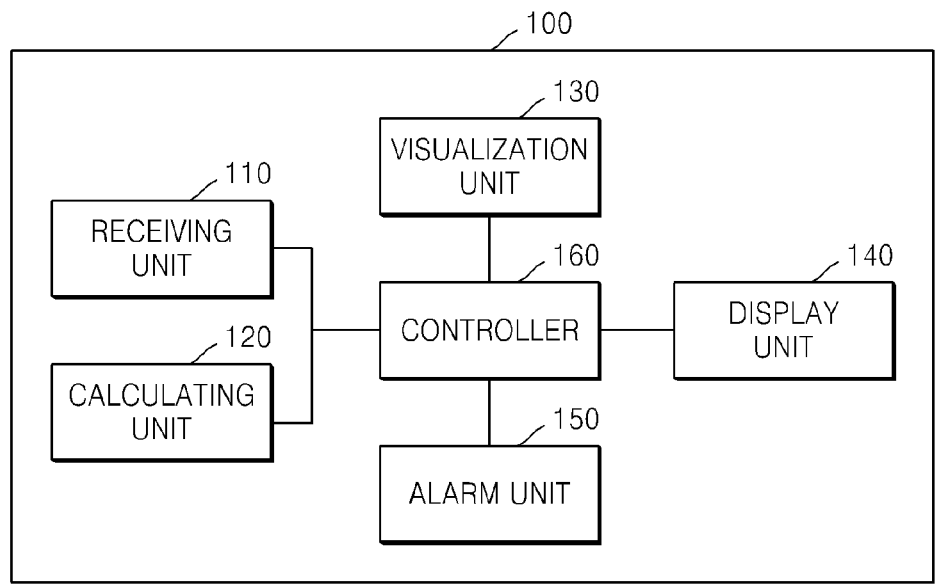
FIG. 1 is a block diagram illustrating a configuration of an ultrasound diagnosis apparatus according to an embodiment of the present invention.

Reference will now be made in detail to embodiments, examples of which are illustrated in the accompanying drawings. Also, while describing the embodiments, detailed descriptions about related well-known functions or configurations that may diminish the clarity of the points of the embodiments of the present invention are omitted. Terms or words used herein shall not be limited to their common or dictionary meanings, and have meanings corresponding to technical aspects of the embodiments of the present invention so as to most suitably express the embodiments of the present invention.

It will be further understood that the terms "comprises' and/or 'comprising,' when used in this specification, specify the presence of stated features, integers, operations, elements, and/or components, but do not preclude the presence or addition of one or more other features, integers, operations, elements, components, and/or groups thereof. The present invention may be described in terms of functional block components and various processing steps. Such functional blocks may be realized by any number of hardware and/or software components configured to perform the specified functions.

A "user" used throughout the specification may include doctors, nurses, medical laboratory technologists, and the like, but the present invention is not limited thereto.

Hereinafter, exemplary embodiments of the present invention will be described in detail with reference to the attached drawings. Like reference numerals designate like elements throughout the specification. In the description, the detailed descriptions of well-known functions and structures may be omitted so as not to hinder the understanding of the present invention. As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram illustrating a configuration of an ultrasound diagnosis apparatus 100 according to an embodiment of the present invention.

As illustrated in FIG. 1, the ultrasound diagnosis apparatus 100 may include a receiving unit 110, a calculating unit 120, a visualization unit 130, a display unit 140, an alarm unit 150, and a controller 160. However, the components illustrated in FIG. 1 are not indispensable components. The ultrasound diagnosis apparatus 100 may include a greater number of components or a less number of components.

The receiving unit 110 may receive a selection of an attenuation coefficient. According to the current embodiment, the selection to the attenuation coefficient may be performed by a user or by the ultrasound diagnosis apparatus 100.

The attenuation coefficient may be a coefficient representing a degree to which an amplitude is decreased when ultrasound spreads in a medium. For example, an attenuation coefficient of water is substantially close to 0, and attenuation coefficients of blood, soft tissues of a human body, and fat are 0.2, 0.5, and 0.6, respectively.

According to the current embodiment, a user or the ultrasound diagnosis apparatus 100 may select an attenuation coefficient based on characteristics of tissues of an object. For example, when main tissues of an object through which ultrasound passes is a soft tissue, a user may select 0.5 as an attenuation coefficient.

The receiving unit 110 may obtain information regarding a contrast agent injected into an object. The contrast agent is a substance which is used in an imaging process to make it easier to see tissues and blood vessels of the body. Examples of the contrast agent of the current embodiment may include an ultrasound contrast agent, micro-bubbles, and the like. The contrast agent of the current embodiment may have a size equal to or smaller than a red blood cell.

The contrast agent may have different vibration characteristics according to manufacturers or products. For example, a contrast agent of a manufacturer A shows a linear vibration characteristic at an acoustic pressure of about 50 kPa and a non-linear vibration characteristic at an acoustic pressure of about 100 kPa, and is broken at an acoustic pressure of more than 150 kPa. On the other hand, a contrast agent of a manufacturer B may be broken at an acoustic pressure of more than 130 kPa.

The receiving unit 110 may receive a selection of a first region which is a region of interest (ROI) in an ultrasound diagnosis region of an object. That is, a user may set a certain region of the ultrasound diagnosis region of the displayed object as an ROI.

The ROI of the current embodiment may be a part in which blood vessels are well-developed. For example, the ROI may be a part including a tumor.

According to the current embodiment, a second region other than the ROI of the ultrasound diagnosis region of the object may be an ultrasound diagnosis region with regard to general tissues where blood vessels are not well-developed. The general tissues refer to normal tissues not including a tumor. Examples of the general tissues may include parenchyma and a normal blood vessel.

The calculating unit 120 may calculate an MI with respect to a depth value in an axis direction in which the ultrasound diagnosis apparatus 100 transmits ultrasound. For example, the calculating unit 120 may calculate the MI based on the following Formula 1, $$MI = \frac{P_{r,a}(Z_{MI}) f_{awf}^{-1/2}}{C_{MI}} \quad (1)$$

wherein, $C_{MI}$=1 MPa·MHz-½, and $Pr,a(Z_{MI})$ denotes attenuated peak-rarefactional acoustic pressure at a depth value ZMI. The $f_{awf}$ denotes an acoustic-working frequency of the ultrasound diagnosis apparatus 100.

The depth value ZMI is obtained according to IEC 62369, which is an international standard of image diagnosis equipment.

According to a standard for real-time display of thermal and mechanical acoustic output indices on diagnostic ultrasound equipment revision 2, an MI in each operation mode is calculated by the following Formula 2 and Formula 3.

1) MI for Pulsed DTPs $$MI_{cw}(LDTP, V_{LDTP}) = \quad (2)$$

$$\frac{\text{Voltage\_Interp}\{MI\_at\_Pii \cdot 3\_Depth(V_{LDTP}, MDTP)\} \times \text{Interp\_HC\_adj\_factor\_MI}\left\{\begin{array}{l}\text{NEMA\_FcMHz}(MDTP), \\ \text{HalfCycles}(LDTP)\end{array}\right\}}{\text{Interp\_HC\_adj\_factor\_MI}\left\{\begin{array}{l}\text{NEMA\_FcMHz}(MDTP), \\ \text{HalfCycles}(MDTP)\end{array}\right\}} \times$$

$$\sqrt{SysAcousticNormFactor(Freq_{(LDTP)})} \times$$
$$\sqrt{XderAcousticNormFactor(Freq_{(LDTP)})}$$

2) MI for CW DTPs:

$$MI_{CW}(LDTP, V_{LDTP}) = \quad (3)$$

$$\text{Voltage\_Interp}\{MI\_at\_Pii \cdot 3\_Depth(V_{LDTP}, MDTP)\} \times$$
$$\sqrt{SysAcousticNormFactor(Freq_{(LDTP)})} \times$$
$$\sqrt{XderAcousticNormFactor(Freq_{(LDTP)})}$$

The calculating unit 120 may calculate MIs with respect to a depth value along a beam direction axis according to the above-defined Formulas.

According to the current embodiment, the calculating unit 120 may continuously calculate an MI with respect to all depth values, or alternatively, the calculating unit 120 may select some depth values and calculate MIs with respect to only the selected depth values, and the non-calculated MIs may be interpolated using the calculated MIs.

According to the current embodiment, the calculating unit 120 may calculate acoustic pressure or a thermal index (TI). Methods of calculating acoustic pressure and a TI would have been obvious to one of ordinary skill in the art and thus a detailed description thereof is not provided.

According to the current embodiment, a TI may include a Soft tissue TI (TIs), a Bone TI (TIb), and a Cranial bone TI (TIc). Accordingly, the calculating unit 120 may individually calculate the TIs, the TIb, and the TIc, or alternatively, may calculate only the TI by selecting a representative TI among the TIs, the TIb, and the TIc.

The calculating unit 120 may calculate a thermal dose. The thermal dose refers to a value obtained by accumulating temperature effects of locations according to time. Accordingly, the calculating unit 120 may accumulate the thermal dose while tracking a varying location by using a motion tracking method.

The calculating unit 120 may calculate the MI in consideration of the attenuation coefficient selected by a user or the ultrasound diagnosis apparatus 100.

The visualization unit 130 may generate an MI map in which a relationship between the calculated MI and a depth value is visualized in the form of a graph, which will be described in detail with reference to FIG. 3.

By performing such a visualization process, a maximum MI value of LDTPs may be visualized based on the following Formula 4.

$$Ispta, 3, sc(STOC) = \frac{MAX}{active\_LDTPs}[MI(LDTP, V_{LDTP})] \quad (4)$$

Alternatively, MIs, which are not calculated during the process for calculating the MIs of the calculating unit 120 and during the process for visualizing the MIs, may be calculated by the following Formula 5, which is different from a linear interpolation, $$MI@depth\langle x\rangle(LDTP, V_{LDTP}) = \quad (5)$$

$$\text{Voltage\_Interp}\{MI\_at\_depth\langle x\rangle(V_{LDTP}, MDTP)\} \times$$

$$\frac{\text{Interp\_HC\_adj\_factor\_MI}\left\{\begin{array}{l}\text{NEMA\_FcMHz}(MDTP), \\ \text{HalfCycles}(LDTP)\end{array}\right\}}{\text{Interp\_HC\_adj\_factor\_MI}\left\{\begin{array}{l}\text{NEMA\_FcMHz}(MDTP), \\ \text{HalfCycles}(MDTP)\end{array}\right\}} \times$$

$$\frac{\sqrt{SysAcousticNormFactor(Freq_{LDTP}))} \times}{\sqrt{XderAcousticNormFactor(Freq_{LDTP}))}}$$

wherein, MIs with respect to depth values other than some depth values in which MIs are calculated may be calculated by using a formula $P_{r,3}/\sqrt{F_c}$ with respect to the MIs of the calculated depth values. In Formula 5, MI@<x> denotes a value obtained by calculating an MI of a depth value x by using the formula $P_{r,3}/\sqrt{F_c}$.

The visualization unit 130 may selectively perform visualization of acoustic pressure and/or visualization of a TI corresponding to a depth value. In this regard, the visualization unit 130 may visualize an MI map, an acoustic pressure map, and a TI map in the form of a two-dimensional or a three-dimensional graph.

Also, the visualization unit 130 may generate a thermal dose map in which the calculated thermal dose is visualized in the form of a graph. For example, the visualization unit 130 may generate a thermal dose map by colors or in the form of a contour or a mesh by accumulating a TI value according to a depth value, a scan line, and time for a predetermined period of time.

The visualization unit 130 may generate an acoustic pressure map including a threshold value according to a vibration characteristic of a contrast agent injected into an object. The threshold value may include at least one of a linear vibration threshold value, a non-linear vibration threshold value, and a breaking vibration threshold value.

Also, the threshold value may be represented by a line, a region, or color in the acoustic pressure map. For example, the visualization unit 130 may represent a linear vibration section, a non-linear vibration section, and a breaking vibration section in green, yellow, and red colors, respectively.

The display unit 140 may display a result of a map visualized in the form of a graph by the visualization unit 130. In this regard, the display unit 140 may selectively display one or two of three interest index maps, that is, MI, acoustic pressure, TI maps, or may display all the interest index maps.

The display unit 140 may be configured as a monitor of a general ultrasound diagnosis apparatus or a user interface, as required.

When a display mode is a single mode, the display unit 140 may display an interest index, that is, an MI, acoustic pressure, or a TI, together with an ultrasound image on a certain region.

Alternatively, when a display mode is a dual mode, an ultrasound image and an interest index may be individually displayed on a screen.

Also, the display unit 140 may provide an enlarged image with respect to a certain part of the ultrasound image or a certain part of the interest index.

According to the current embodiment, the display unit 140 may selectively display at least one of a TIs map, a TIb map, and a TIc map. Also, the display unit 140 may selectively display the TI map and the thermal dose map.

According to the current embodiment, the display unit 140 may display at least one of one-, two-, and three-dimensional maps with respect to an MI, acoustic pressure, and a TI, or may display at least one of a contour map, a gray map, a mesh map, and a color map.

The display unit 140 may output an ultrasound image of blood vessel tissues including the contrast agent with respect to the first region, which is an ROI, and may output an ultrasound image of general tissues with respect to the second region.

The alarm unit 150 may output an alarm signal when the calculated MI or acoustic pressure value exceeds a predetermined value. For example, when the MI is close to 1.9, which is an international standard, the alarm unit 150 may output the alarm signal. In this case, a user may protect an object by controlling a transmission output.

Alternatively, the alarm unit 150 may output an alarm signal even when the calculated MI or acoustic pressure value is less than a predetermined scope.

For example, when the MI is less than 1.3, the alarm unit 150 may output the alarm signal. In this case, a user may increase a transmission output to obtain a high-definition ultrasound image.

The alarm signal may include at least one of an image signal, a vibration signal, and a voice signal. That is, according to the current embodiment of the present invention, the alarm unit 150 may visually inform that an interest index deviates from a predetermined scope through an image signal including a certain shape, a certain color, an alert message, or the like. Alternatively, the interest index may generate a vibration signal when an interest index deviates from a predetermined scope. Alternatively, the alarm unit 150 may output a voice signal including an alert message, an alert bell, or the like.

According to the current embodiment, the alarm unit 150 may apply a color map to an interest index map so as to visually show the meaning of an alert clearly according to a degree to which an interest index is close to a predetermined reference value. For example, as the interest index approaches a reference value, the alarm unit 150 may apply a red color to a map, and as interest index deviates the reference value, the alarm unit 150 may apply a blue color to a map.

The controller 160 may set an acceptable range of an interest index. For example, the controller 160 may set the acceptable range of the interest index based on a user's input or may set an acceptable range automatically according to an international standard. The controller 160 may set the acceptable range of the interest index to be lower than an international standard with respect to a certain object based on a diagnosis breakdown and medical information.

According to the current embodiment, the controller 160 may control a transmission voltage by controlling an ultrasound output part (not shown). For example, the controller 160 may control the transmission voltage based on an attenuation coefficient selected by a user or the ultrasound diagnosis apparatus 100.

Also, the controller 160 may control the transmission voltage based on a threshold value according to a vibration characteristic of a contrast agent injected into the object. Since most of the ultrasound contrast agent is broken after a breaking vibration threshold value, the controller 160 may control the transmission voltage so as not to break the contrast agent and to maintain a non-linear vibration characteristic.

The controller 160 may control a transmission voltage of the first region to a first transmission voltage so as to maintain an MI or an acoustic pressure value in the first region, which is an ROI, within a predetermined threshold range. For example, when the first region is a part including a tumor having blood vessels into which a contrast agent is injected well-developed and when a contrast agent is used, the controller 160 may control a transmission voltage of the first region to the first transmission voltage at which a contrast agent is not broken and a non-linear vibration characteristic is maintained so as to maintain a low MI environment.

The controller 160 may control a transmission voltage of the second region other than the ROI to be below the first transmission voltage. Since the second region is a region out of a user's interest, image sensitivity of the second region does not need to be high. Accordingly, in order to prevent a contrast agent from being broken, the transmission voltage of the second region may be set to be lower than that of the first region.

Also, the controller 160 may control overall operations of the receiving unit 110, the calculating unit 120, the visualization unit 130, the display unit 140, and the alarm unit 150.

Figure 2:
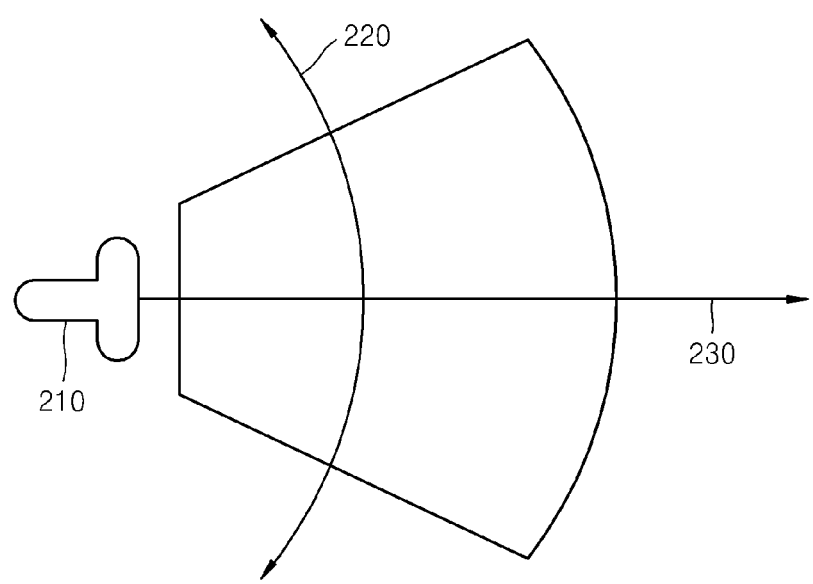
FIG. 2 is a conceptual diagram illustrating a reference axis for calculating an interest index and displaying a map of the interest index according to an embodiment of the present invention.

FIG. 2 is a conceptual diagram illustrating a reference axis for calculating an interest index and displaying a map of the interest index according to an embodiment of the present invention.

A direction in which ultrasound is transmitted from a transmission transducer 210 of the ultrasound diagnosis apparatus 100 and travels may be an axis of a depth value 230. The transmission transducer 210 may be included in a probe.

The axis of the depth value 230 may start from a boundary surface of an object to be diagnosed using the ultrasound diagnosis apparatus 100 and may correspond to a direction in which the depth value 230 increases inward a soft tissue.

The probe may transmit an ultrasound beam, which is generated due to transmitted pulse signals that are properly input to be delayed, to an object along a scan line 220. In this case, the ultrasound diagnosis apparatus 100 may form a two- or three-dimensional map based on interest index values corresponding to the depth value 230 and the scan line 200.

According to the current embodiment, the probe may be at least one of 1 dimension (1D), 1.5D, and 2D (matrix) probes.

Figure 3:
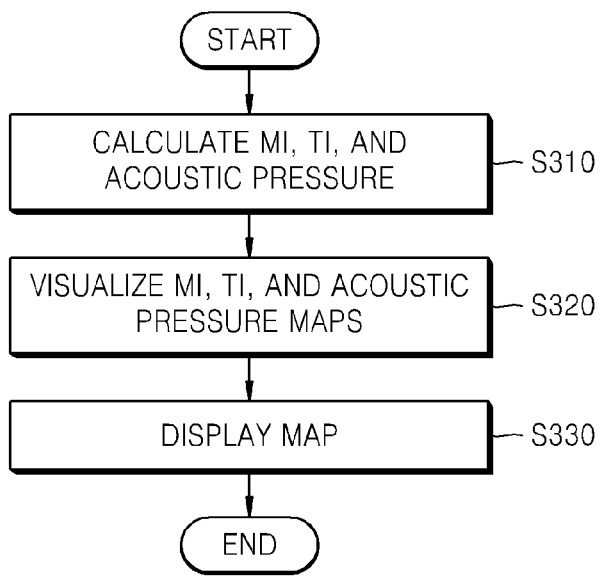
FIG. 3 is a flowchart illustrating a method of operating an ultrasound diagnosis apparatus, according to an embodiment of the present invention.

FIG. 3 is a flowchart illustrating a method of operating the ultrasound diagnosis apparatus 100, according to an embodiment of the present invention.

According to the current embodiment, the ultrasound diagnosis apparatus 100 may calculate interest indexes, that is, an MI, a TI, and an acoustic pressure, corresponding to depth values in a direction in which ultrasound travels from an ultrasound output part of the transmission transducer 210 (S310). The ultrasound diagnosis apparatus 100 may calculate only the MI, and may selectively calculate the acoustic pressure and the TI. The MI may be calculated by Formulas 1 to 5 as described above. Also, methods of calculating the acoustic pressure and the TI would have been obvious to one of ordinary skill in the art and thus a detailed description thereof is not provided.

According to the current embodiment, the ultrasound diagnosis apparatus 100 may select a plurality of depth values and directly calculate the MI by applying the above-defined Formulas 1 to 4 only to the selected depth values, for example, 1, 2.3, 3.1, 4.2, 5.5, and the like. In this case, the ultrasound diagnosis apparatus 100 may apply a proper interpolation method, for example, a linear interpolation method or an interpolation method according to Formula 5, to the MI corresponding to non-calculated depth values in a direction in which non-calculated ultrasound travels. According to the current embodiment, an interpolation method may also be applied to calculate a TI and acoustic pressure.

According to the current embodiment, a user or the ultrasound diagnosis apparatus 100 may select an attenuation coefficient based on characteristics of tissues of an object. In general, the tissues of an object includes blood, soft tissue, and fat that are mixed with one another, and thus, a user or the ultrasound diagnosis apparatus 100 may select an attenuation coefficient by analyzing main components of tissues of the object.

The ultrasound diagnosis apparatus 100 may calculate an MI in consideration of the selected attenuation coefficient. A relationship between the MI and the attenuation coefficient may be obtained with reference to Formula 1. For example, Pr.3 denotes a value obtained by calculating acoustic pressure Pr measured in a water tank filled with water at an attenuation rate of 0.3 dB.

Accordingly, when the ultrasound diagnosis apparatus 100 selects a high attenuation coefficient, the ultrasound diagnosis apparatus 100 may further increase a transmission voltage, thereby increasing the sensitivity of an ultrasound image.

According to the current embodiment, the ultrasound diagnosis apparatus 100 may calculate a thermal dose. A thermal dose display does not simply display a varying temperature value and displays TI values by colors or in the form of a contour or a mesh by accumulating the TI value according to a depth value, a scan line, and time for a predetermined period of time, and thus, changes in temperature of an object due to ultrasound may be effectively seen.

Figure 4:
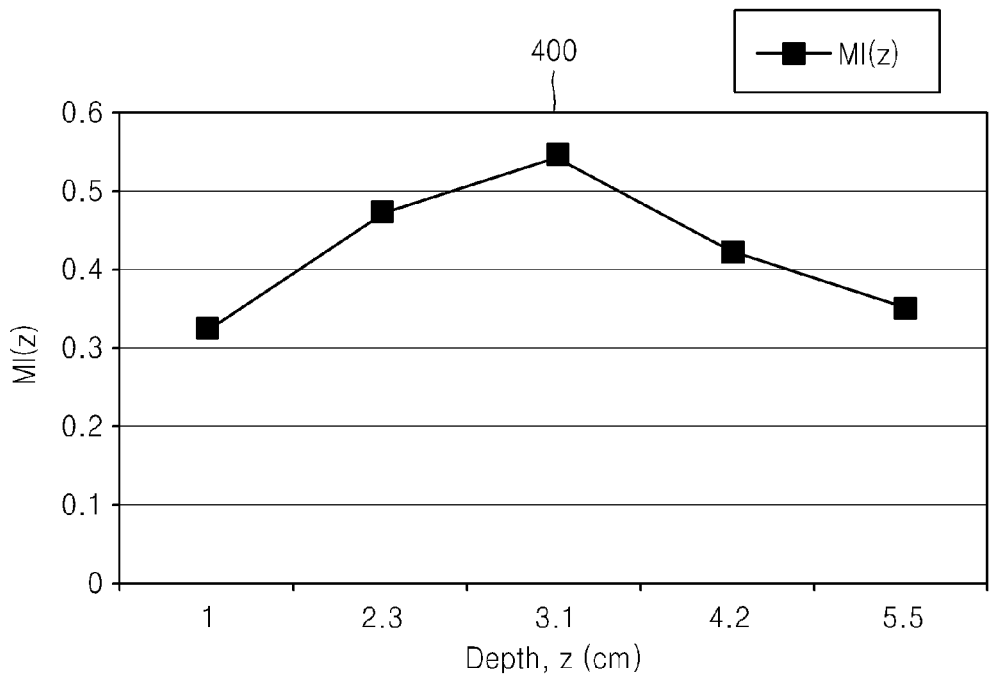
FIG. 4 is a graph showing a mechanical index (MI) map displayed according to an embodiment of the present invention.

The ultrasound diagnosis apparatus 100 may generate an interest index map in which a relationship between a depth value and the calculated interest index (that is, the MI, the acoustic pressure, the TI, and the thermal dose) that is visualized in the form of a graph (S320). For example, as illustrated in FIG. 4, the MI may vary according to the depth value.

According to the current embodiment, since the ultrasound diagnosis apparatus 100 uses a focus beam, the MI may have a maximum value at a depth value being focused. Also, even in an acoustic pressure map, a similar result to the MI map illustrated in FIG. 4 may be obtained. Although a TI map may have a similar shape to the MI map or the acoustic pressure map, a TI may have a maximum value at a depth value lower than the depth value being focused.

According to the current embodiment, the ultrasound diagnosis apparatus 100 may generate an interest index map as a 1D, 2D, or 3D map. For example, when the ultrasound diagnosis apparatus 100 uses a 1D probe, the ultrasound diagnosis apparatus 100 may generate the interest index map as a 2D map by calculating interest indexes corresponding to the depth value 230 and the scan line 220. In this case, the ultrasound diagnosis apparatus 100 may generate a 3D map by representing the interest indexes corresponding to the depth value 230 and the scan line 220 sterically in the form of a mesh. Alternatively, the ultrasound diagnosis apparatus 100 may represent the interest index map that varies according to time (frame) without being fixed during ultrasound scanning. That is, the ultrasound diagnosis apparatus 100 may generate a 3D map by calculating interest indexes according to the depth value 230, the scan line 220, and time.

When the ultrasound diagnosis apparatus 100 uses a 1.5D probe or a 2D (matrix) probe, the ultrasound diagnosis apparatus 100 may represent interest indexes of three directions of axial (a depth value), lateral (a scan line), and elevation in the form of a 3D map.

Figure 5:
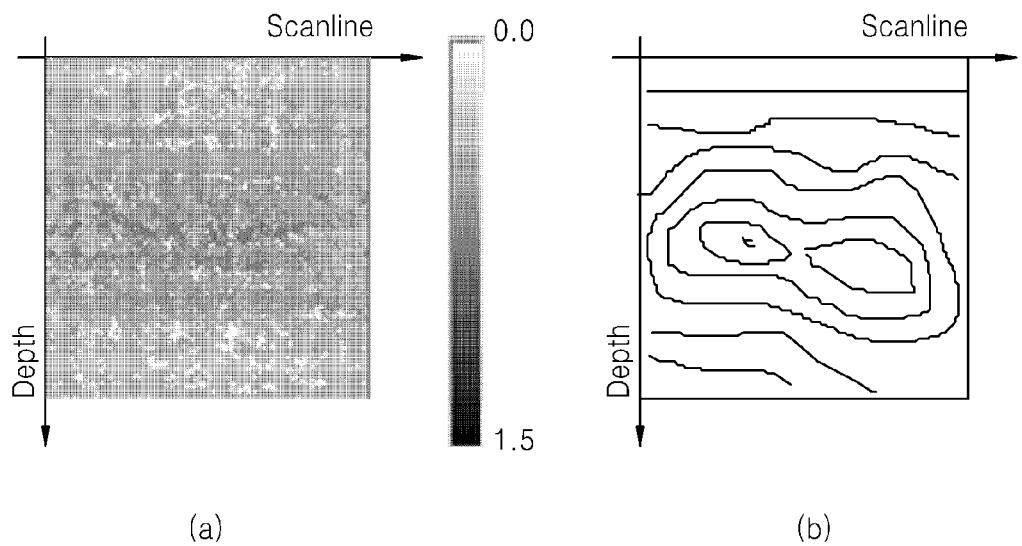
FIG. 5 is a view illustrating a two-dimensional MI map displayed according to an embodiment of the present invention.

The ultrasound diagnosis apparatus 100 may represent an interest index map as various maps, for example, a contour map, a gray map, a mesh map, a color map, or the like. For example, as illustrated in FIG. 5A, the ultrasound diagnosis apparatus 100 may generate a 2D map as a gray scale with respect to the depth value 230 and the scan line 220. Also, as illustrated in FIG. 5B, the ultrasound diagnosis apparatus 100 may generate a 2D map in the form of a contour.

According to the current embodiment, the ultrasound diagnosis apparatus 100 may display the interest index maps, that is, the MI, acoustic pressure, and TI maps, by using the display unit 140 (S330).

When the interest index map is a TI map, the display unit 140 may display TIs, TIb, and TIc maps as one TI map. In this case, the display unit 140 may designate different colors to the TIs, TIb, and TIc maps or represent lines with different thicknesses for easy distinction.

Alternatively, the display unit 140 may display a certain TI map that is arbitrarily selected by a user among the TIs, TIb, and TIc maps.

Also, the ultrasound diagnosis apparatus 100 may not easily determine whether an object being diagnosed is a soft tissue, a bone, or a cranial bone, and thus, the maximum map among the TIs, TIb, and TIc maps may be selected as a representative TI map and displayed.

According to the current embodiment, the ultrasound diagnosis apparatus 100 may represent an interest index map in various ways, for example, in the form of a 1D, 2D, or 3D map. Accordingly, a user may easily see a degree to which interest indexes are distributed, and may visually check whether each interest index exceeds an acceptable reference value based on map information and may also check regions where the interest indexes exceed the acceptable reference value.

Also, the ultrasound diagnosis apparatus 100 may combine two or more maps among a contour map, a gray map, a mesh map, and a color map that are generated with respect to an interest index and may display the combined map.

According to the current embodiment, the ultrasound diagnosis apparatus 100 may display a threshold value according to a vibration characteristic of a contrast agent together with an acoustic pressure map.

Figure 6:
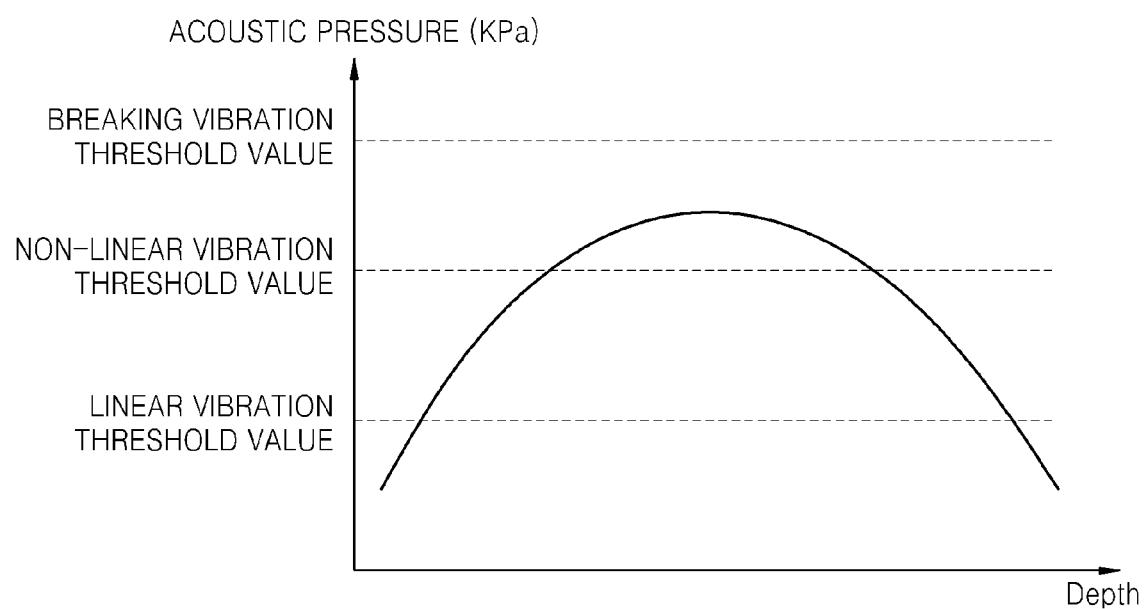
FIG. 6 is a graph for showing an acoustic pressure map according to an embodiment of the present invention.

For example, as illustrated in FIG. 6, the ultrasound diagnosis apparatus 100 may display the threshold value of the contrast agent on the acoustic pressure map according to a depth value. The contrast agent linearly vibrates between 0 and a linear vibration threshold value and non-linearly vibrates between the linear vibration threshold value and a non-linear vibration threshold value. Also, the contrast agent non-linearly vibrates after the non-linear vibration threshold value, and at the same time, a rate at which the contrast agent is broken starts to be increased after the non-linear vibration threshold value, and thus, most of the contrast agent is broken after a breaking vibration threshold value.

Accordingly, a user may control a transmission voltage so as not to break the contrast agent and to maintain a non-linear vibration characteristic by checking the threshold value according to the vibration characteristic of the contrast agent provided by the ultrasound diagnosis apparatus 100.

According to the current embodiment, the threshold value may be represented by colors or lines.

Figure 7:
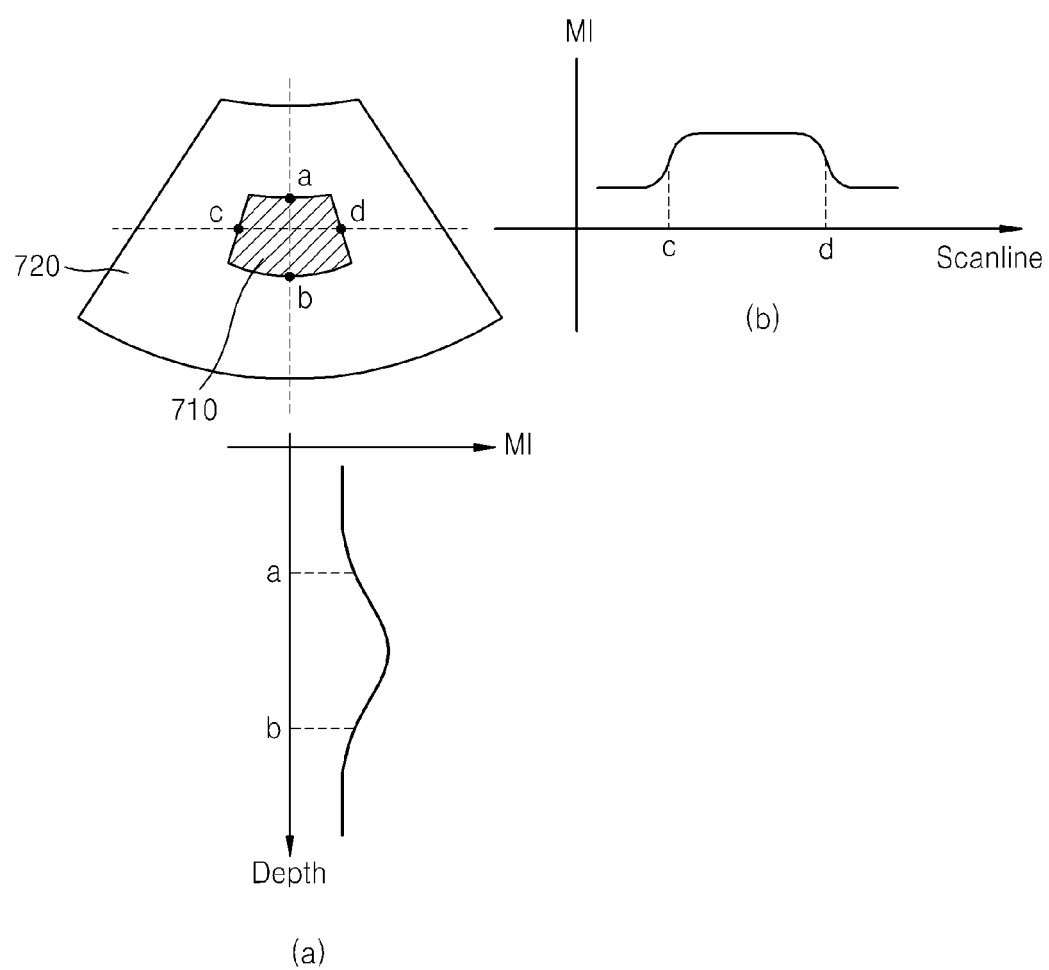
FIG. 7 is a view illustrating an MI map in a region of interest according to an embodiment of the present invention.

FIG. 7 is a view illustrating an MI map in an ROI according to an embodiment of the present invention.

As illustrated in FIG. 7, a user may set a first region 710, which is an ROI, in an ultrasound diagnosis image. For example, when an object includes a tumor, the user may set a part including the tumor as the first region 710, which is the ROI, in order to determine whether the tumor is a benign or malignant tumor.

According to the current embodiment, under an environment using a contrast agent, the ultrasound diagnosis apparatus 100 may differently control MIs or acoustic pressures of the first region 710 and a second region 720 other than the ROI in the ultrasound diagnosis image.

The ultrasound diagnosis apparatus 100 may obtain an ultrasound image from the first region 710 by stimulating and vibrating the used contrast agent, and may obtain an ultrasound image from the second region 720 by using an MI or acoustic pressure having a degree at which the contrast agent is rarely broken. That is, the ultrasound diagnosis apparatus 100 may set a transmission voltage of the second region 720 to be lower than that of the first region 710.

In this case, an ultrasound image may be obtained from the second region 720 other than the first region 710, which is an ROI, by using an MI or acoustic pressure having a degree at which the contrast agent is rarely broken, and thus, a rate at which the contrast agent is broken may be significantly decreased.

FIG. 7A illustrates an MI of an ROI according to a depth value. Since the ultrasound diagnosis apparatus 100 uses a focus beam, when the focus beam is focused on the ROI, an MI in the first region 710, which is the ROI, may be a maximum.

FIG. 7B illustrates an MI of an ROI according to a scan line. As illustrated in FIG. 7B, an MI of a scan line in the first region 710 may be higher that in the second region 720. In other words, according to the current embodiment, ultrasound image sensitivity in the ROI may be strategically increased.

The ultrasound diagnosis apparatus 100 may output an ultrasound image of blood vessel tissues including a contrast agent with respect to the first region 710 and may output an ultrasound image of general tissues with respect to the second region 720.

Embodiments of the present invention include a computer-readable recording medium including program commands for executing operations implemented through various computers. The computer-readable recording medium can store program commands, data files, data structures, or combinations thereof. The program commands recorded in the computer-readable recording medium may be specially designed and configured for the present invention or be known to those skilled in the field of computer software. Examples of a computer-readable recording medium include magnetic media such as hard disks, floppy disks, and magnetic tapes, optical media such as CD-ROMs and DVDs, magneto-optical media such as floptical disks, or hardware devices such as ROMs, RAMs, and flash memories, which are specially configured to store and execute program commands. Examples of the program commands include a machine language code created by a compiler and a high-level language code executable by a computer using an interpreter and the like. The above-described hardware apparatus may be configured to operate as at least one software module in order to perform operations of the present invention.

According to the current embodiment, an interest index, for example, an MI, acoustic pressure, a TI, and the like, according to depths of a ultrasound diagnosis part may be provided to a user or a health professional in the form of a map, and thus, the user or the health professional may visually check whether the interest index exceeds an international acceptable reference value and may check regions where the interest index exceeds the acceptable reference value.

Also, a user may control a transmission output so as to maintain an international acceptable reference value of an interest index and to maximize image quality.

According to the current embodiment, in an ultrasound diagnosis apparatus using a contrast agent or micro-bubbles, information capable of performing a precision adjustment regarding using of the contrast agent or the micro-bubbles may be provided to a user. Accordingly, the user may adjust acoustic pressure so as to maximize the quality of an ultrasound image without breaking the micro-bubbles.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound diagnosis apparatus comprising:
a controller configured to calculate a thermal index (TI) corresponding to a depth value in a direction in which ultrasound travels from an ultrasound output part of a transmission transducer and a thermal dose obtained by accumulating the TI according to the depth value, a scanline value, and time, and generate a thermal dose map in which the calculated thermal dose is visualized in the form of a graph;
a display configured to display the thermal dose map; and
a receiver configured to receive a user input for selection a particular attenuation coefficient,
wherein the controller controls a transmission voltage based on the particular attenuation coefficient, tracks a varying location using a motion tracking method, and calculates the thermal dose at the varying location by accumulating the TI values tracked at the varying location over time,
wherein the varying location is defined by using the depth value and the scanline value,
wherein the controller is further configured to calculate a mechanical index (MI) and an acoustic pressure value corresponding to depth values in a direction in which ultrasound travels from the ultrasound output part of the transmission transducer, and generate an MI map in which a relationship between the calculated MI and the depth value is visualized in the form of a graph and an acoustic pressure map in which a relationship between the calculated acoustic pressure value and the depth value is visualized in the form of a graph,
wherein the receiver is configured to receive selection of a first region, which is a region of interest (ROI), in a ultrasound diagnosis region of an object, and
wherein the controller is further configured to control a transmission voltage of the first region to a first transmission voltage so as to maintain an MI or an acoustic pressure value in the first region within a predetermined threshold range and control a transmission voltage of a second region so that a transmission voltage of the second region other than the ROI in the ultrasound diagnosis region of the object is below the first transmission voltage.

2. The ultrasound diagnosis apparatus of claim 1, wherein the controller selects a plurality of the depth values, calculates TIs respectively corresponding to the plurality of depth values, and interpolates non-calculated TIs corresponding to depth values in a direction in which ultrasound travels by using TIs corresponding to the calculated depth values.

3. The ultrasound diagnosis apparatus of claim 1, wherein the display is further configured to selectively display the MI map or the acoustic pressure map.

4. The ultrasound diagnosis apparatus of claim 1, wherein the display further displays at least one selected from the group consisting of a Bone TI (TIb) map, a Cranial bone TI (TIc) map, and a Soft tissue TI (TIs) map.

5. The ultrasound diagnosis apparatus of claim 1, wherein the controller further outputs an alarm signal when the calculated MI or the calculated acoustic pressure value exceeds a predetermined range.

6. The ultrasound diagnosis apparatus of claim 5, wherein the alarm signal comprises at least one selected from the group consisting of an image signal, a vibration signal, and a voice signal.

7. The ultrasound diagnosis apparatus of claim 1, wherein the MI map or the acoustic pressure map is a two-dimensional or three-dimensional map.

8. The ultrasound diagnosis apparatus of claim 1, wherein the MI map or the acoustic pressure map comprises at least one selected from the group consisting of a contour map, a gray map, a mesh map, and a color map.

9. The ultrasound diagnosis apparatus of claim 1, wherein the controller calculates an MI corresponding to a depth value in consideration of the particular attenuation coefficient.

10. The ultrasound diagnosis apparatus of claim 9, wherein the attenuation coefficient is selected based on characteristics of tissues of an object.

11. The ultrasound diagnosis apparatus of claim 1, wherein the receiver is further configured to obtain information regarding a contrast agent injected into an object, and the controller generates an acoustic pressure map including a threshold value due to a vibration characteristic of the contrast agent injected into the object.

12. The ultrasound diagnosis apparatus of claim 11, wherein the threshold value comprises at least one selected from the group consisting of a linear vibration threshold value, a non-linear vibration threshold value, and a breaking vibration threshold value.

13. The ultrasound diagnosis apparatus of claim 11, wherein the controller is further configured to control the transmission voltage based on a threshold value due to a vibration characteristic of the contrast agent injected into the object.

14. The ultrasound diagnosis apparatus of claim 1, wherein the display outputs an ultrasound image of blood vessel tissues comprising a contrast agent with respect to the first region, and outputs an ultrasound image of general tissues with respect to the second region.

15. A method of operating an ultrasound diagnosis apparatus, the method comprising:

calculating a thermal index (TI), a mechanical index (MI) and an acoustic pressure value corresponding to a depth value in a direction in which ultrasound travels from an ultrasound output part of a transmission transducer, and a thermal dose obtained by accumulating the TI according to the depth value, a scanline value, and time;

generating a thermal dose map in which the calculated thermal dose is visualized in the form of a graph, an MI map in which a relationship between the calculated MI and the depth value is visualized in the form of a graph and an acoustic pressure map in which a relationship between the calculated acoustic pressure value and the depth value is visualized in the form of a graph;

displaying the thermal dose map;

receiving a user input for selection a particular attenuation coefficient;

controlling a transmission voltage based on the particular attenuation coefficient;

receiving selection of a first region, which is a region of interest (ROI), in a ultrasound diagnosis region of an object;

controlling a transmission voltage of the first region to a first transmission voltage so as to maintain an MI or an acoustic pressure value in the first region within a predetermined threshold range; and controlling a transmission voltage of a second region so that a transmission voltage of the second region other than the ROI in the ultrasound diagnosis region of the object is below the first transmission voltage, wherein the calculating of the thermal dose comprises a varying location using a motion tracking method and calculating the thermal dose at the varying location by accumulating the TI values tracked at the varying location over time, and wherein the varying location is defined by using the depth value and the scanline value.

* * * * *